United States Patent [19]
Denyer et al.

[11] Patent Number: 6,131,568
[45] Date of Patent: Oct. 17, 2000

[54] NEBULIZER

[75] Inventors: Jonathan Stanley Harold Denyer, Pagham; Anthony Dyche, Hants; Paul Stanley Hensey, Horsham, all of United Kingdom

[73] Assignee: Medic-Aid Limited, United Kingdom

[21] Appl. No.: 09/057,184

[22] Filed: Apr. 8, 1998

[30] Foreign Application Priority Data

Feb. 26, 1998 [GB] United Kingdom ................ 9804149

[51] Int. Cl.$^7$ ............................................... A61M 11/00
[52] U.S. Cl. ......................... 128/200.21; 128/200.14
[58] Field of Search .................. 128/200.14, 200.16, 128/200.18, 200.21, 203.12; 239/338, 505, 507, 513, 514

[56] References Cited

U.S. PATENT DOCUMENTS

| 4,396,015 | 8/1983 | Johnson | 128/200.14 |
| 4,429,835 | 2/1984 | Brugger et al. | 239/338 |
| 4,746,067 | 5/1988 | Svoboda | 239/338 |
| 5,209,225 | 5/1993 | Glenn | 128/200.21 |
| 5,355,872 | 10/1994 | Riggs et al. | 128/200.21 |
| 5,503,139 | 4/1996 | McMahon et al. | 128/200.21 |
| 5,584,285 | 12/1996 | Salter et al. | 128/200.21 |
| 5,823,179 | 10/1998 | Grychowski et al. | 128/200.21 |

FOREIGN PATENT DOCUMENTS

| 0711609A2 | 5/1994 | European Pat. Off. . |
| 0627266A2 | 12/1994 | European Pat. Off. . |
| 560190 | 12/1942 | United Kingdom . |
| 1138274 | 12/1968 | United Kingdom . |
| PCT/F188/00176 | 7/1989 | WIPO . |
| PCT/CA97/00096 | 8/1997 | WIPO . |

Primary Examiner—Aaron J. Lewis
Assistant Examiner—Teena Mitchell
Attorney, Agent, or Firm—William A. Simons; Wiggin & Dana

[57] ABSTRACT

A nebulizer comprises a gas exit, at least one outlet adjacent to the gas exit, and a deflector for deflecting a stream of gas issuing from the gas exit over the at least one outlet for drawing a substance to be atomized from it, and for atomizing the substance in the gas. The deflector defines first and second profiles, and the atomizer has an atomizing configuration in which the first profile of the deflector lies in the stream of gas for atomization, and non-atomizing configuration in which the second profile of the deflector lies in the stream of gas without atomization of the substance.

29 Claims, 9 Drawing Sheets

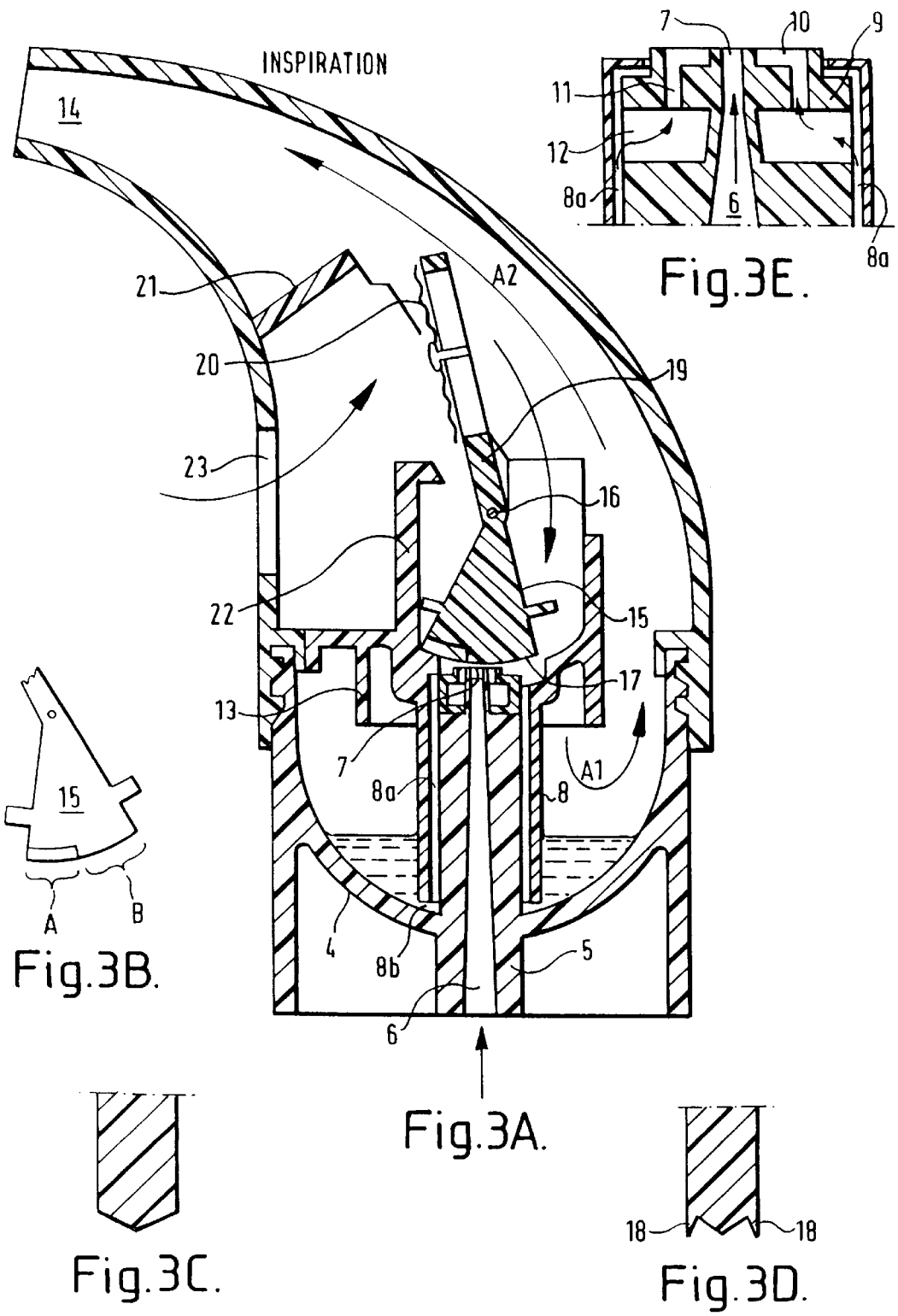

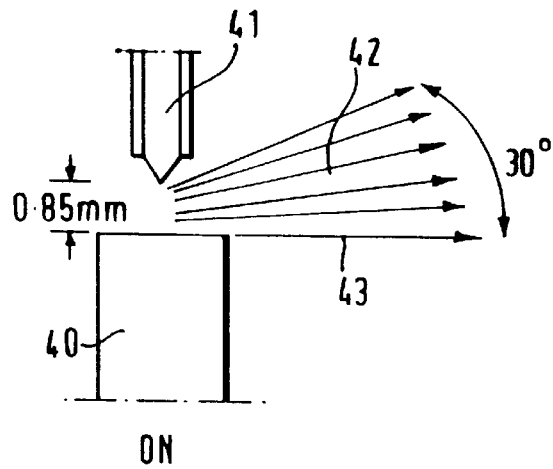
Fig.10A.
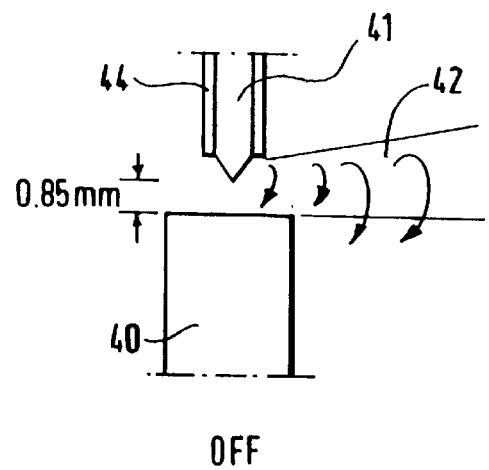
Fig.10B.
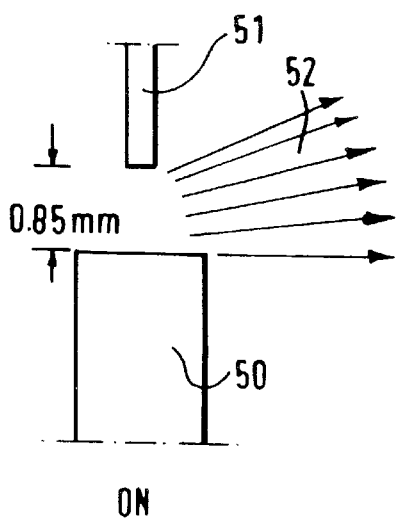
Fig.11.A.
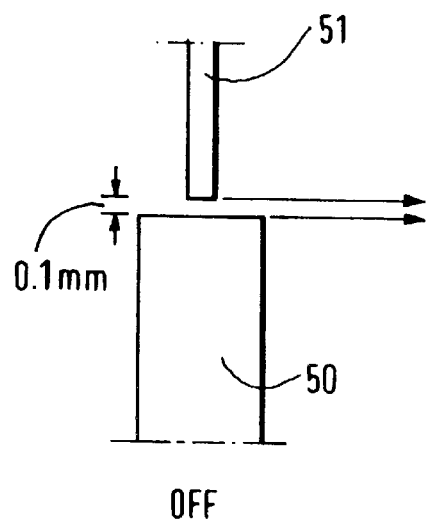
Fig.11.B.

NEBULIZER

BACKGROUND OF THE INVENTION

1. Field of the Invention

The present invention relates to nebulisers, normally used for administering a medicament to a patient by inspiration, the medicament being atomised into very small droplets or particles. Such a nebuliser comprises a gas exit, an outlet adjacent to the gas exit, and a deflector for deflecting a stream of gas issuing from the gas exit over the outlet for drawing a substance to be atomised from it, and for atomising the substance in the gas.

2. Brief Description of the Prior Art

In our earlier patent application EP 95307936.5 (publication number 0711609) we disclosed an atomiser of this kind in which atomisation only takes place during inspiration. This was achieved by the use of a movable deflector. The general principle of operation is shown in FIG. 1, in which gas issues from a gas exit 1 under pressure. An outlet 2 is disposed adjacent the gas exit. The outlet 2 includes a passageway 2a through which the substance to be atomised is led to an annular reservoir 2b which surrounds the gas exit 1. During inspiration, a deflector 3 is located above and in the path of the stream of gas issuing from the gas outline 1. This is shown in FIG. 1A, from which it will be seen that the gas is deflected above the outlet 2. This causes a low pressure region just above the outlet 2 which draws the substance to be atomised up through the passage 2a into the reservoir 2b, and causes the substance within the reservoir 2b to be atomised into the deflected gas stream. The atomised substance is carried away to be inhaled by the patient. As the patient stops inhaling, the deflector 3 swings about its pivot 3a and out of the path of the gas stream (FIG. 1C). The pressurised gas is then not deflected, but is directed straight upwards. No atomisation occurs because the stream of gas is not deflected across the outlet 2, and does not create a low pressure region just above the outlet by which medicament is drawn through the passage 2a.

This atomiser has been found to be extremely effective in using medicament much more efficiently, since atomisation only occurs during inspiration. However, it has been found that, as the deflector 3 moves out of the stream of gas, the liquid that is running along the edge of the deflector is sprayed into the top of the neubliser where it collects, much of it being unable to return to the reservoir, mainly due to the fact that the velocity of the gas emerging from the gas exit is extremely high, in the region of 500 m/sec. Any droplets that are carried up into the neubliser top will tend to shatter, and be further dispersed upon impact with the top. The high velocity gas stream hinders the return of the substance. This is shown in FIG. 1B.

This problem is also experienced by other arrangements, for example, the device shown in WO 97/29799 has the same problem. In this prior art, the outlet 2 is also adjacent to the gas exit 1, and a deflector 3 is used to deflect the stream of gas issuing from the gas exit 1, as shown in FIG. 2. During inspiration, the deflector 3 is located in the position shown in FIG. 2C. The deflector 3 directs the stream of pressurised gas across the outlet 2 causing atomisation. Once inspiration has ceased, the deflector 3 is raised into the upper part of the housing as shown in FIG. 2A. As the deflector is raised, more of the stream of gas passes up the air inlet duct carrying atomised medicament with it, as shown in FIG. 2B, until the device reaches the "off" position of FIG. 2A. The vertical stream of gas causes any liquid in the top of the nebuliser to be held there, rather than to drain back down into the base for re-atomisation.

BRIEF SUMMARY OF THE PRESENT INVENTION

According to a first aspect of the present invention, a nebuliser comprises a gas exit, at least one outlet adjacent to the gas exit, and a deflector for deflecting a stream of gas issuing from the gas exit over the at least one outlet for drawing a substance to be atomised from it, and atomising the substance in the gas, wherein the deflector defines first and second profiles, and in that the atomiser has an atomising configuration in which the first profile of the deflector lies in the stream of gas for atomisation, and a non-atomising configuration in which the second profile of the deflector lies in the stream of gas for atomisation, and a non-atomising configuration in which the second profile of the deflector lies in the stream of gas without atomisation of the substance. In this way, the atomisation of the substance may be "switched" on and off. By maintaining the deflector in the path of stream of gas at all times, the substance is not sprayed into the top of the nebuliser since the deflector deflects the stream of gas away from the top of the nebuliser.

According to one embodiment, the deflector includes the first and second regions, the first region having the first profile and the second region having the second profile. Means for effecting relative movement between the gas exit and the deflector, such that the first region and the second region of the deflector selectively lie in the stream of gas, may be included. By including a means sensitive to a patient's breathing for controlling the said movement effecting means, the first region of the deflector can be arranged to lie in the stream of gas during inspiration of a patient, and the second region of the deflector can be arranged to lie in the stream of gas when inspiration is not occurring. Thus, atomisation will only occur during inspiration, and during exhalation a substance will not be forced into the top of the nebuliser.

According to a preferred form of his embodiment, the deflector is movable relative to the gas exit. Preferably, the deflector includes a deflector edge, the edge including the first and second regions. It is also preferred that the edge of the deflector is arc-shaped.

According to another embodiment, the deflector comprises first and second elements such that, when the atomiser is in the atomising configuration, the first element is located in the stream of gas and forms the first profile; and, when the atomiser is moved to the non-atomising configuration, the first and second elements move relative to each other so as to form, together, the second profile of the deflector. This means that only one of the elements needs to move in order to "switch" to atomisation on and off.

Preferably, a means sensitive to a patient's breathing is included for controlling the relative movement of the elements so that the first profile of the deflector lies in the stream of gas during inspiration of a patient, and a second profile of the deflector lies in the stream of gas when inspiration is not occurring. The second element may be a sleeve disposed around at least a substantial part of the first element. The sleeve may project ahead of the first element when the deflector is placed in its second configuration. Alternatively, the first element may be a bar, and the second element is moveable into position adjacent to the bar. Preferably, this is a position protruding ahead of the bar. The second element may be pivotally mounted for movement, and the second element may be positioned at both sides of the bar.

In all embodiments, the second profile of the deflector typically includes edge extensions extending from the extremities of the deflector generally towards the gas exit. These extensions may be of less than one millimeter in length.

According to a second aspect of the invention, a nebuliser comprises a gas exit; at least one outlet adjacent the gas exit; and a deflector for deflecting a stream of gas issuing from the gas exit over the at least one outlet for drawing a substance to be atomised from it, and for atomising the substance in the gas, wherein the deflector is adjustable between an atomising configuration in which the deflector lies in the stream of gas for atomisation, and a non-atomizing configuration in which the deflector lies in the stream of the gas to increase the deflection of at least a portion of the stream of gas so that no atomisation occurs.

According to a third aspect, the invention is a method of atomising a substance using a deflector for diverting a stream of gas emerging from a gas exit over at least on outlet of the substance characterised by changing the profile of the deflector between a first profile in which atomisation takes place, and a second profile in which atomisation does not occur, but in which the deflector remains in the path of the stream of gas.

According to a fourth aspect, the invention is a method of atomising a substance using a deflector for deflecting a stream of gas emerging from a gas exit over at least one outlet, of the substance, wherein the adjustment of the deflector between an atomising configuration in which the deflector lies in the stream of gas for atomisation, and a non-atomising configuration in which the deflector lies in the stream of gas and increases the deflection of at least a portion of the stream of gas so that no atomisation occurs. Embodiments of the present invention are described below by way of example only and with reference to drawings in which:

BRIEF DESCRIPTION OF THE DRAWINGS

FIGS. 3A to 3E show a nebuliser according to the present invention during the inspiration phase;

FIG. 10 shows, schematically, a typical way in which the stream of gas might be deflected, and FIG. 11 show, schematically, a further embodiment in which deflection of the stream of gas may be changed.

DETAILED DESCRIPTION OF PREFERRED EMBODIMENTS OF THE PRESENT INVENTION

Figure 1A:
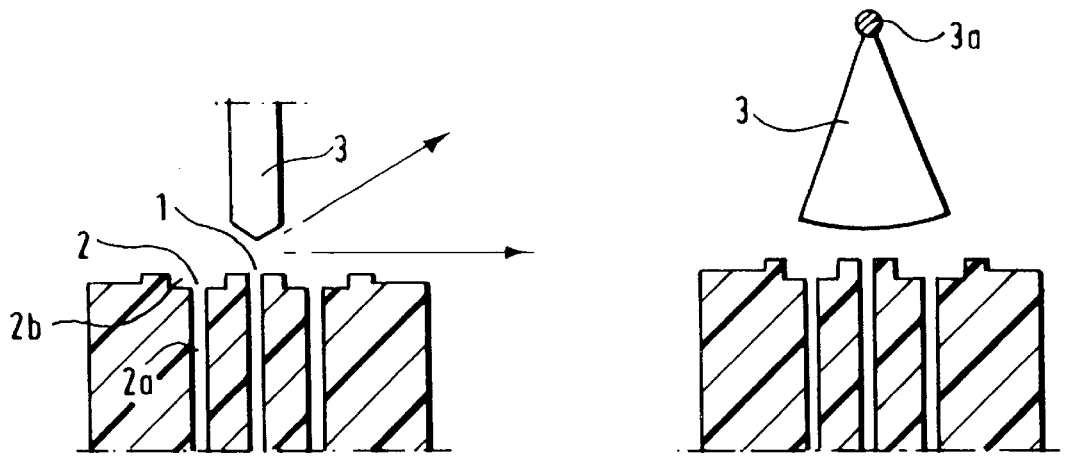
FIG. 1 shows a prior art arrangement in three positions.
Figure 1B:
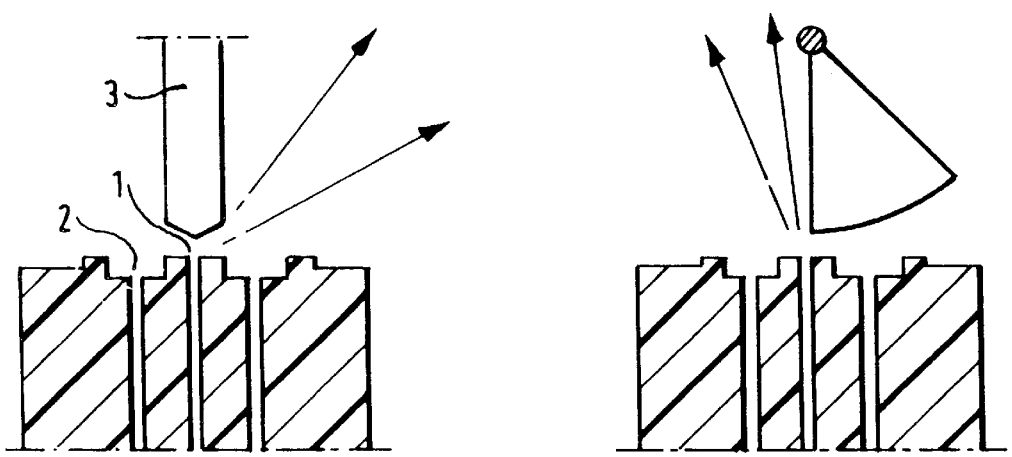
Figure 1C:
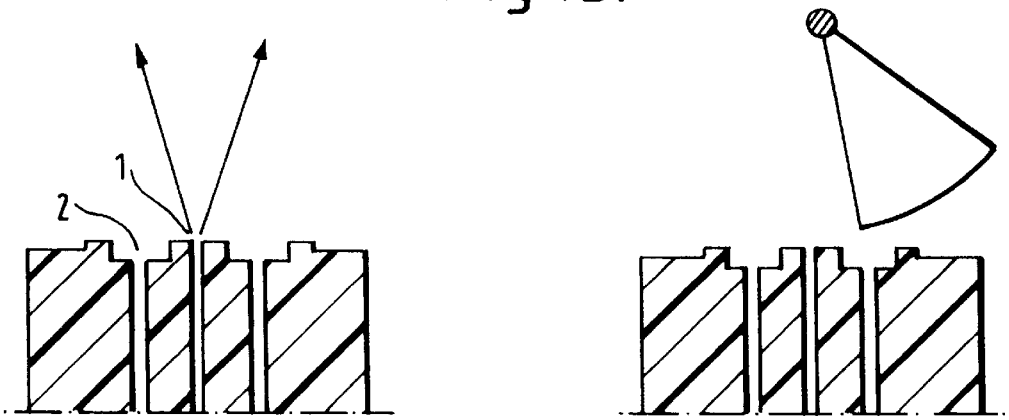
Figure 2A:
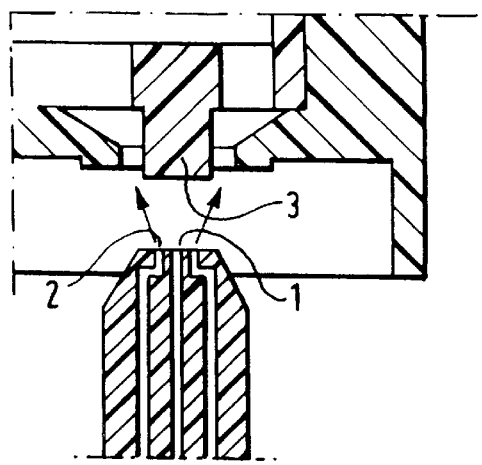
FIG. 2 shows another prior art arrangement in three positions.
Figure 2B:
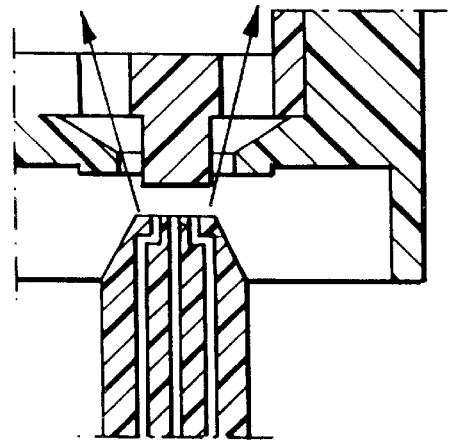
Figure 2C:
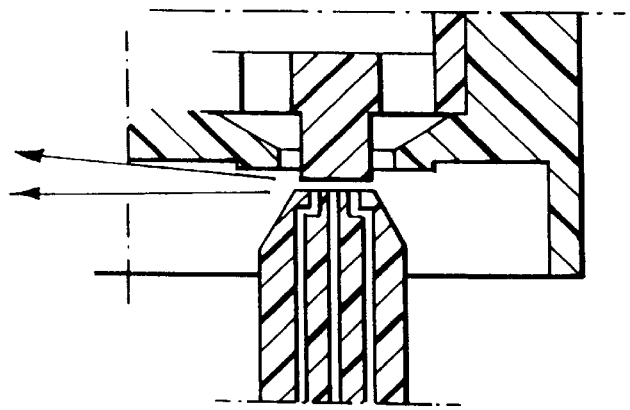
Figure 4A:
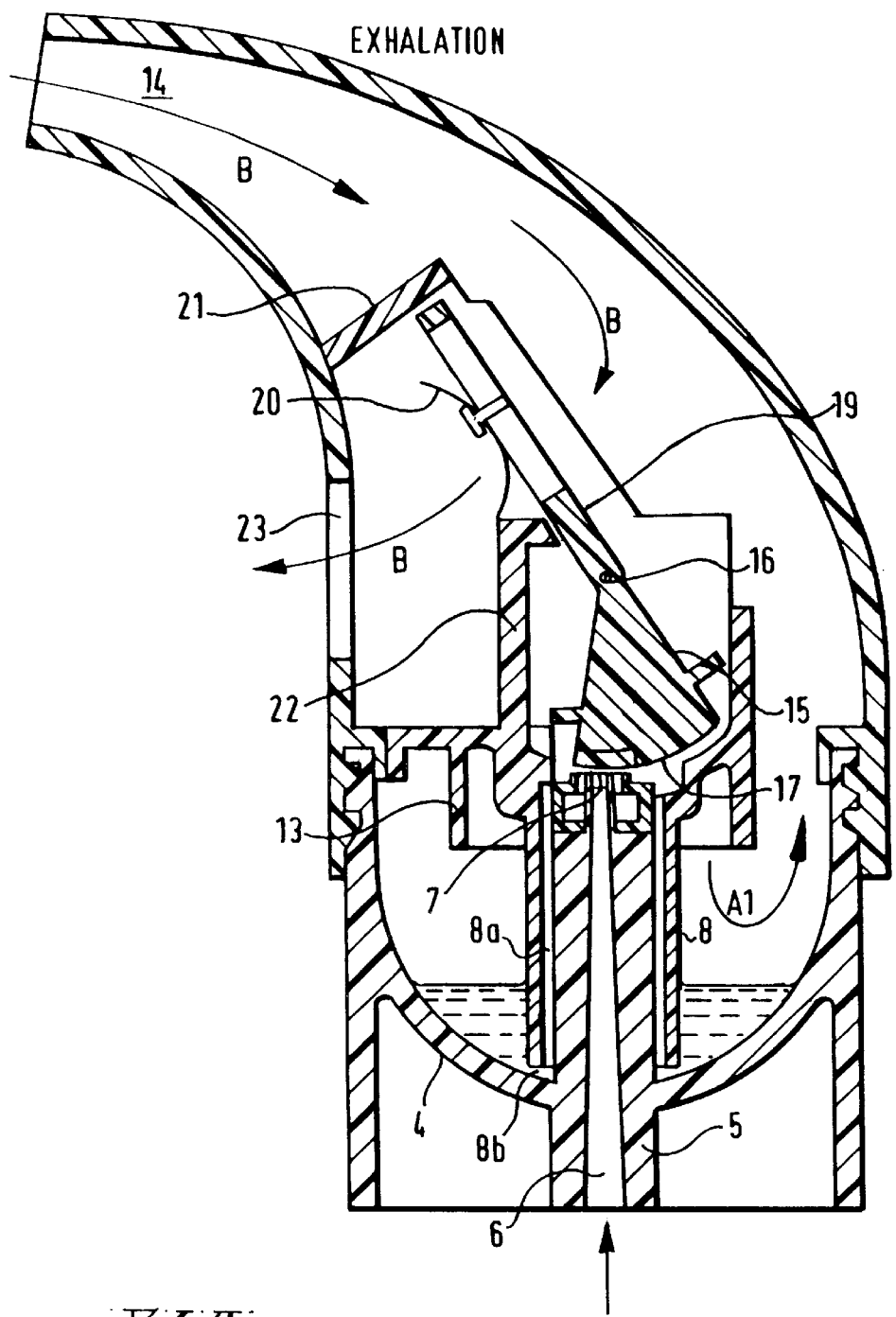
FIG. 4 shows the nebuliser of FIG. 3 during an exhalation phase.
Figure 4B:
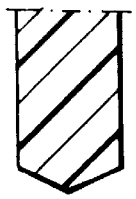
Figure 4C:
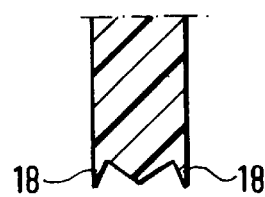

Referring first to the embodiment shown in FIGS. 3 and 4, FIG. 3A shows an assembled nebuliser, including a bowl 4 through which passes a gas pipe 5 which defines a gas passage 6. Gas is passed up the gas passage 6 under pressure to a gas exit 7 shown in more detail in FIG. 3E. A sleeve 8 is disposed around the gas pipe 5 with a space 8a inside it between the sleeve and the gas pipe. A space 8b also exists between the lower end of the sleeve 8 and the bowl 4 to allow medicament to enter the space 8A. The gas pipe 5 terminated in a head 9 from which the gas emerged under pressure from the gas exit 7. In the top of the head 9, an annular reservoir 10 surrounds the gas exit 7. Below the annular reservoir 10, several medicament passageways 11 lead from a medicament chamber 12. Before use, the bowl 4 is filled with medicament, and this is drawn up between the gas pipe 5 and the sleeve 8 into the medicament chamber 12, through the medicament passageways 11 into the annular reservoir 10. Surrounding the head 9 is a downwardly directed baffle 13 beneath which medicament-laden air must pass before passing upwards towards a mouthpiece 14 and as indicated by arrows A1 and A2 in FIG. 3A.

Above the head 9 is located a deflector 15 which is a flat plate-like element shaped as a sector of a circle. At its top-end, it is hinged at a pivot 16 and at its lower end, which has a curved lower edge 17, it lies in the path of a stream of gas emerging from the gas exit 7. This lower edge 17 includes two regions shown in FIG. 3B as A and B, each of which has a different cross-sectional profile. The cross-sectional profile of region B is shown in FIG. 3C, and is generally pointed. However, the cross-sectional profile of region A of the lower edge is shown in FIG. 3D, and includes edge extensions 18 which point downwardly generally towards the gas exit 7.

A flap 19 is carried by the top of the deflector 15 and pivots about he pivot 16 with the deflector 15. The flap 19 contains a one-way valve 20 through which air can pass in one direction. The flap 19 contains a one-way valve 20 through which air can pass in one direction. The flap 19 is also seatable against walls 21 and 22 between which air may pass to and from a vent 23. When the flap 19 is open, air is able to pass from atmosphere through the vent 23 into the mouthpiece 14.

Figure 5:
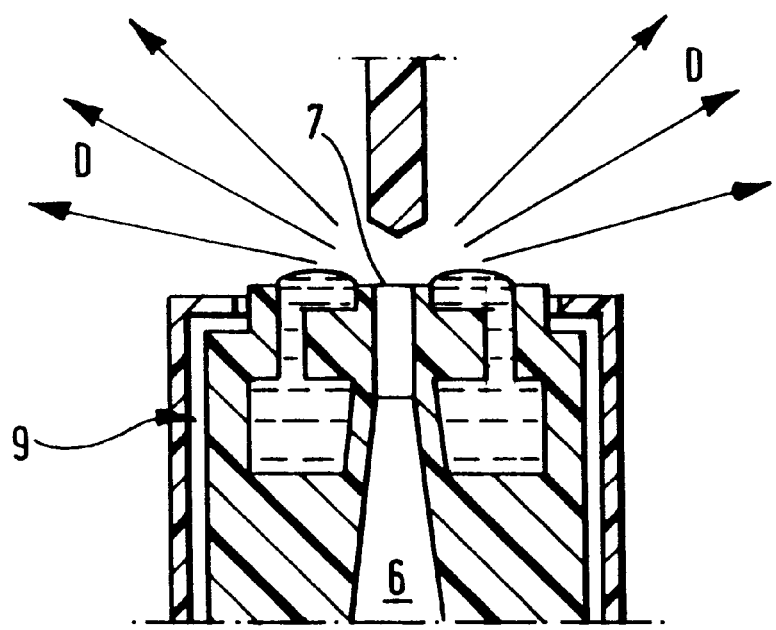
FIG. 5 shows the a cross-sectional view of the gas exit and deflector of FIG. 4 during inspiration.

FIG. 3A shows the nebuliser during inspiration by a patient through the mouthpiece 14. The inspiration causes a drop in pressure within the mouthpiece 14, causing the flap 19 to open, and ambient air to pass into the nebuliser via the vent 23. The opening of the flap 19 causes the deflector 15 to be placed in the position shown in FIG. 3A in which region B of the curved lower edge 17 is placed directly in the stream of gas emerging from the gas exit 7. This causes the gas to be deflected, as shown by the arrows D in FIG. 5, over the top of the annular reservoir 10. This creates low pressure just above the reservoir 10, thereby drawing medicament from the bowl 4 into the reservoir via the spaces 8A and 8B. Since the velocity of the stream of gas emerging from the gas exit 7 is extremely high, typically about 500 m/sec, the medicament is drawn from the reservoir 10 and is atomised into a fine mist of droplets. The deflection of gas by the deflector 15 also causes air to be drawn downwards past the deflector to the region above the head 9, where it entrains the atomised medicament, and then passes downwards beneath the downwardly directed baffle 13 and back up around the outside of the baffle and upwards through the mouthpiece 14 to the patient.

Figure 6:
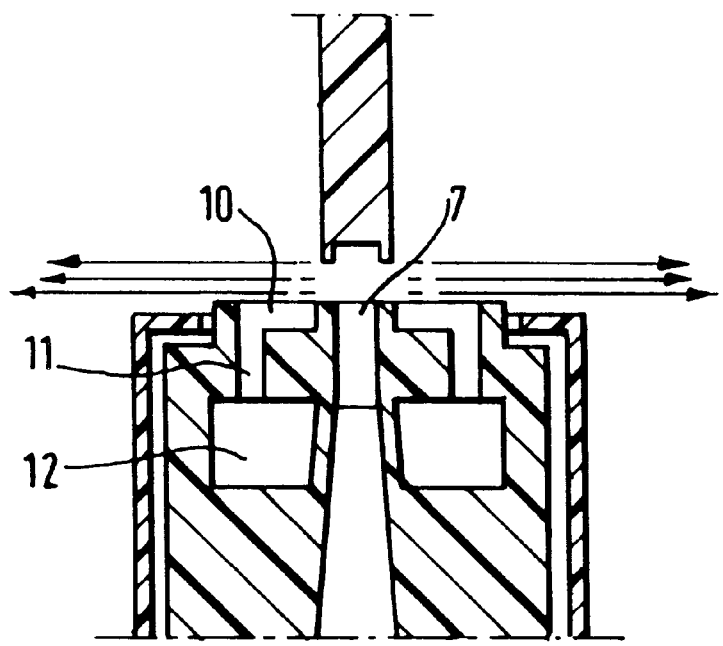
FIG. 6 is a cross-sectional view of the gas exit and deflector of FIG. 4 during exhalation.

During the exhalation, as shown in FIG. 4A, the flap 19 closes against the walls 21 and 22 and the one-way valve 20 opens allowing the exhaled air to pass freely to atmosphere via the vent 23 as shown by arrows B. The closure of the flap 19 causes the deflector 15 to be moved into the position shown in FIG. 4A where the stream of gas impacts on the region A of the lower edge 17 shown in FIG. 4C. This causes the deflected air to pass over the reservoir 10 in such a manner that the medicament is not drawn up from the bowl 4, and is not atomised by the air as is shown in FIG. 6. This is achieved by the edge extensions 18 since no low pressure region is created just above the reservoir 10. The deflected air is changed from when it is deflected during inhalation, and at least a portion of the deflected air is deflected through an increased angle and this typically causes the whole of the deflected air to be disrupted and/or deflected through an increased angle to prevent atomisation. In addition, as the deflector 15 moves from the position shown in FIG. 3A to the position shown in FIG. 4A, the stream of gas continues to be deflected, and is not directed upwardly into the top of the nebuliser, or into the mouthpiece 14. Preferably, the deflector 15 is biased towards the position shown in FIG. 4A so that atomisation only takes place during inspiration.

Figure 7A:
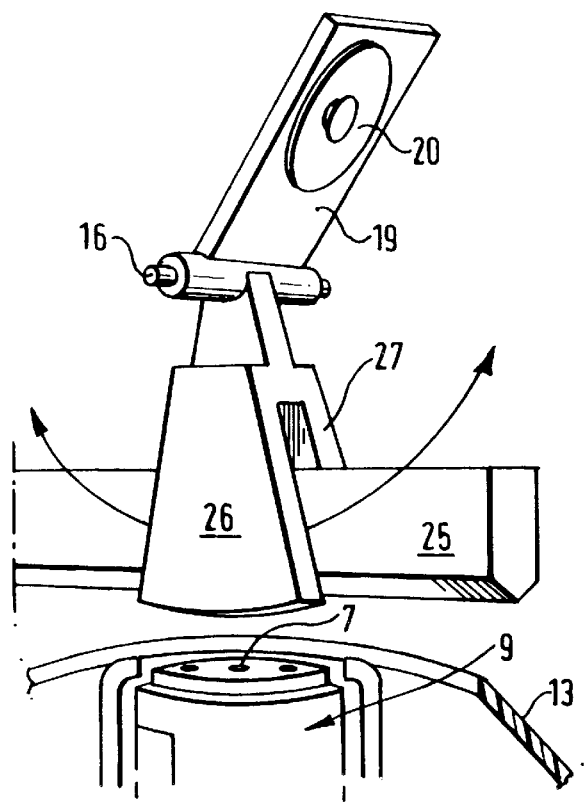
FIGS. 7A to 7E show another embodiment by which this invention may be carried out; including swinging arms.
Figure 7B:
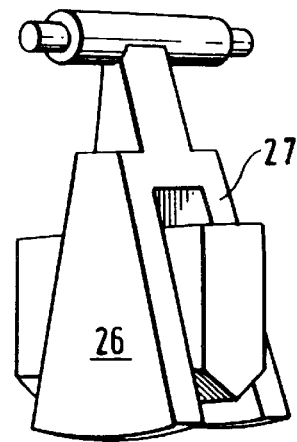
Figure 7C:
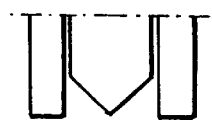
Figure 7D:
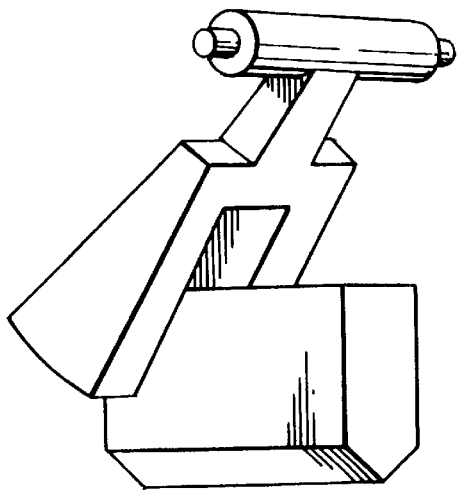
Figure 7E:
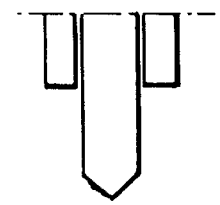

Referring now to FIGS. 7A and 7E, another form of deflector is shown which may replace the deflector of FIGS. 3A and 4A. In FIG. 7A, the deflector includes a bar 25 which is positioned above the gas exit 7. The bar 25 is generally pointed. The flap 19 is pivoted about a pivot 16 just as in FIG. 3A. However, the flap 19 carries two arms 26 and 27 which swing about the pivot 16 with the flap. The arms 26 and 27 are positions on either side of the bar 25. During exhalation, the arms 26 and 27 lie on either side of the part of the bar 25 on which the stream of gas impacts. The arms 26 and 27 are a little longer than the edges of the bar 25 as shown in FIGS. 7B and 7C. This causes the stream of gas to be dispersed above the reservoir 10 in such a way that no atomisation takes place. The medicament is neither drawn up from the bowl 4 nor atomised. Thus, the bar 25 and the arms 26, 27 act together to deflect the stream of gas. During inspiration, the flap 19 is moved so as to cause the arms 26, 27 to swing away from the part of the bar 25 on which the stream of gas impacts. The generally pointed profile of the bar 25 directs the stream of gas over the reservoir 10 in such a manner that medicament is drawn from the bowl 4 and is atomised by that stream of gas. In effect, the arms 26, 27 are retracted as shown in FIGS. 7D and 7E. Thus, when inspiration ceases, the stream of gas is not directed at great velocity into the top the nebuliser.

Figure 8:
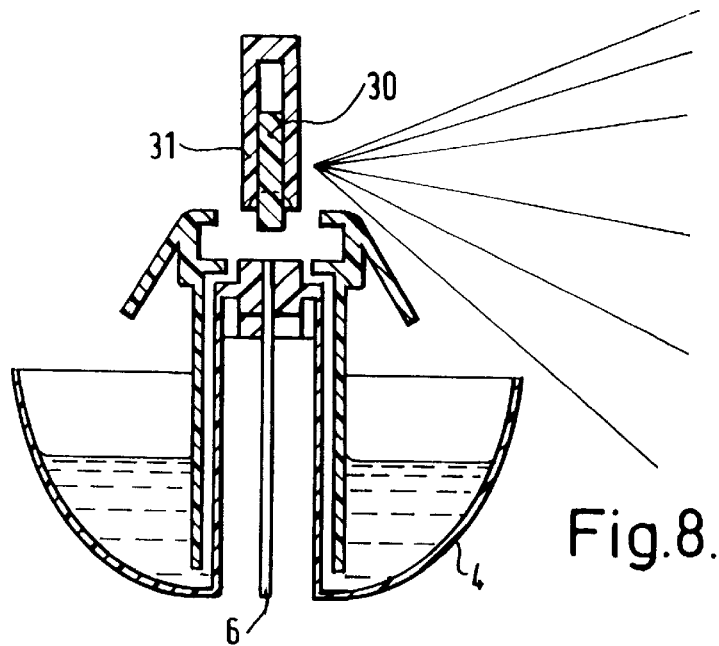
FIG. 8 shows a further embodiment by which the deflector is retractable inside a sleeve.
Figure 8A:
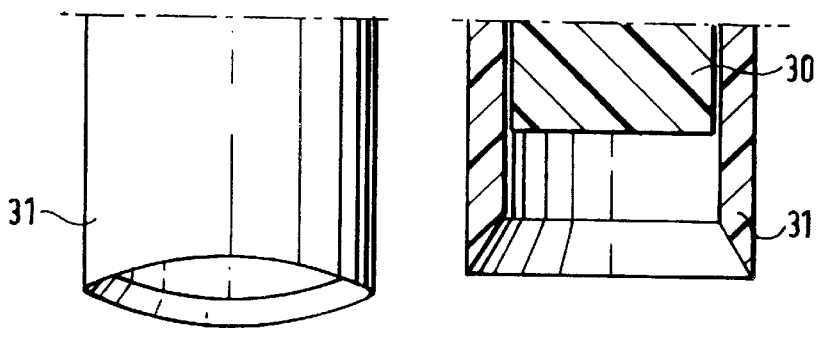
Figure 8B:
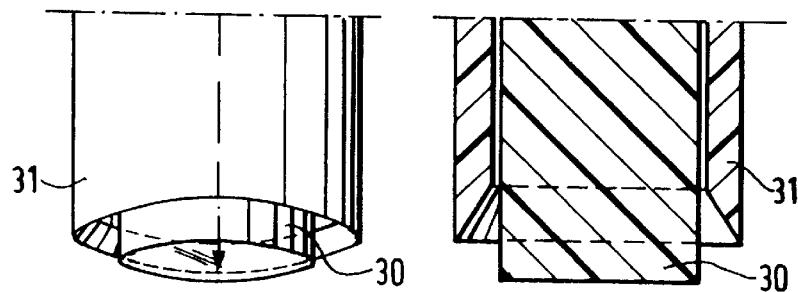
Figure 8C:
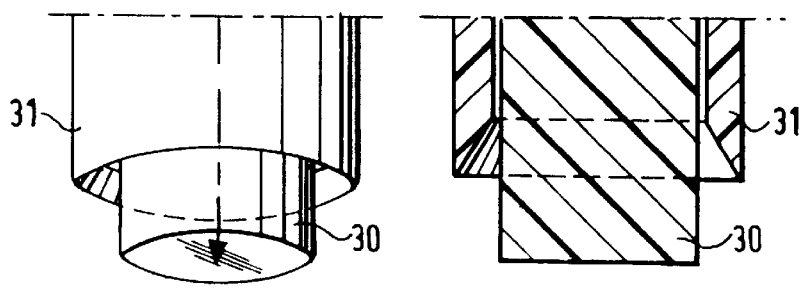

Referring now to FIG. 8, the deflector is arranged somewhat differently. In this case, the deflector 30 is circular, or 'pin'-shaped and is retractable into a sleeve 31. When the deflector 30 is extended from the sleeve 31, as shown in the bottom part of FIG. 8, atomisation takes place, since the stream of gas is deflected over a reservoir 10. As the deflector 30 is retracted into the sleeve 31, nebulisation ceases owing to the sleeve 31 projecting downwards further than the deflector 30. Thus, in the bottom view of FIG. 8, the deflector 30 deflects the stream of gas, whereas in the top view of FIG. 8, both the deflector 30 and the sleeve 31 act together to increase the deflection of at least a portion of the deflected gas relative to gas deflected during inhalation. Typically, the portion of increased deflection gas causes the whole of the deflected gas to be disrupted and/or increased in deflection.

Figure 9:
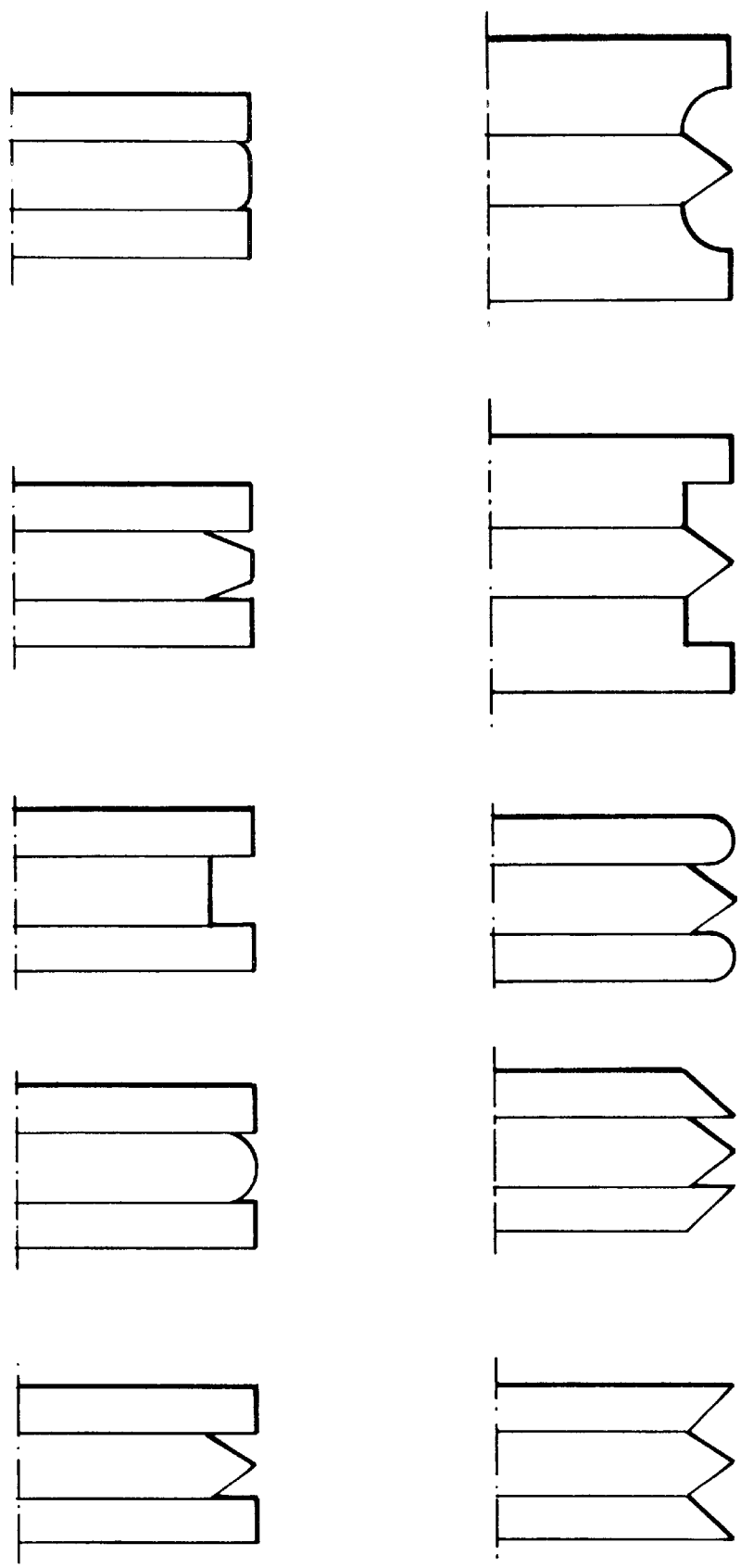
FIG. 9 shows a variety of deflector profiles which should result in non-atomisation when placed in the path of a stream of gas.

FIG. 9 shows a number of difference deflector profiles which might be used to stop atomisation. Clearly, the characteristics of these shapes will vary. It will be noted that most of the shapes includes edge extensions which we presently find need to be no more than 0.5–1.0 mm in order to stop atomisation.

Various different deflector profiles may be used in order to obtain atomisation, including V-shaped bars, wedges, plain bars and various domes, pips and pins.

FIG. 10 is a schematic view showing the head 40 from which a stream of gas emerges. For clarity, the gas exit and the reservoir are not shown. What is shown, however, is the deflector 41 and an envelope 42 of the deflected gas. The envelope 42 diverges at an angle of about 30°. The lower edge 43 of the envelope 42 is generally horizontal, and causes medicament to be drawn out from the reservoir and atomised into the air. In the second part of FIG. 10, the deflector 41 also includes side pieces 44 which typically serve to disrupt and/or increase the deflection of the envelope 42. This destroys any negative pressure just above the medicament outlet. Thus, atomisation does not take place in this position.

Referring to FIG. 11, the head 50 is shown from which a stream of gas emerges. For clarity, the gas exit and the reservoir are not shown. The deflector 51 is disposed in the path of the stream of gas which emerges from the gas exit, and the deflected gas is indicated generally at 52. The deflected gas 52 causes medicament to be drawn out from the reservoir and atomised into the air. In the second part of FIG. 11, the deflector 51 is moved downwards towards the gas exit so as to increase the deflection of at least a portion of the deflected air when compared with the deflected air in the first part of FIG. 11. This typically causes the whole of the deflected air to be disrupted and/or increased in deflection. This destroys any negative pressure just above the medicament outlet. Thus, atomisation does not take place in this position. As indicated in FIG. 11, the deflector 51 is moved from a position of about 0.85 mm from the gas outlet where atomisation takes place, to a position about 0.1 mm from the gas outlet whereby atomisation does not take place. It should be noted that, in this embodiment, the deflector 51 does not actually close the gas exit, but merely disrupts the gas emerging from the exit.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A nebulizer comprising:

a gas exit;

at least one outlet adjacent the gas exit; and a deflector for deflecting a steam of gas issuing from the gas exit over at least one of said outlets for drawing a substance to be atomized from it, and for atomizing the substance in the gas;

wherein the deflector defines first and second profiles, and in that the nebulizer has an atomizing configuration in which the first profile of the deflector lies in the stream of gas for atomization, and a non-atomizing configuration in which the second profile of the deflector lies in the stream of gas without atomization of the substance and the first profile differs from the second profile.

2. A neublizer according to claim 1 wherein the deflector comprises first and second elements such that when the atomizer is in the atomizing configuration, the first element is located in the stream of gas and forms the first profile, and when the atomizer is moved to the non-atomizing configuration, the first and second elements move relative to each other so as to form, together, the second profile of the deflector.

3. A nebulizer according to claim 2 wherein the first element is moveable.

4. A nebulizer according to claim 2 wherein the second element is moveable.

5. A nebulizer according to claim 2 further comprising means sensitive to a patient's breathing for controlling the relative movement of the elements so that the first profile of the deflector lies in the stream of gas during inspiration of a patient, and the second profile of the deflector lies in the stream of gas when inspiration is not occurring.

6. A nebulizer according to claim 5 wherein the second element is a sleeve disposed around a substantial part of the first element.

7. A nebulizer according to claim 6, wherein the sleeve projects from the first element when the deflector is placed in its second configuration.

8. A nebulizer according to claim 5 wherein the means sensitive to a patient's breathing is a flap.

9. A nebulizer according to claim 8 wherein the flap is a flap valve which when a patient inhales, is opened and places the first profile of the deflector in the stream of gas.

10. A nebulizer according to claim 9 wherein the flap valve is biased towards its closed position.

11. A nebulizer according to claim 2 wherein the first element is a bar, and the second element is moveable into position adjacent the bar.

12. A nebulizer according to claim 11 wherein the second element is moveable into a position extending a short distance ahead of the bar in the direction of the gas outlet.

13. A nebulizer according to claim 12 wherein the second element is mounted for pivotal movement.

14. A nebulizer according to claim 13 wherein the second element is shaped like a sector of a circle.

15. A nebulizer according to claim 14 wherein the second element is positioned at both sides of the bar.

16. A nebulizer according to claim 1 wherein the second profile of the deflector includes edge extension extending from the extremities of the deflector generally towards the gas exit.

17. A nebulizer according to claim 16 wherein the edge extensions extend forward by less than one millimeter.

18. A nebulizer comprising:
 a gas exit;
 at least one outlet adjacent the gas exit; and
 a deflector for deflecting a stream of gas issuing from the gas exit over at least one of said outlets for drawing a substance to be atomized from it, and for atomizing the substance in the gas, wherein the deflector is adjustable between an atomizing configuration in which the deflector lies in the stream of gas for atomization, and non-atomizing configuration in which the deflector lies in the stream of the gas to increase the deflection of at least a portion of the stream of gas so that no atomization occurs.

19. A nebulizer according to claim 18 wherein the deflector defines first and second profiles, and in that the first profile of the deflector lies in the stream of gas when the deflector is in the atomizing configuration, and the second profile of the deflector lies in the stream of gas when the deflector is in the non-atomizing configuration.

20. A nebulizer according to claim 19 wherein the deflector includes first and second regions, the first region having the first profile and the second region having the second profile.

21. A nebulizer according the claim 20 further comprising means for effecting relative movement between the gas exit and the deflector such that the first region and the second region of the deflector selectively lie in the stream of gas.

22. A nebulizer according to claim 21 further comprising means sensitive to a patient's breathing for controlling the said movement effecting means so that the first region of the deflector lies in the stream of gas during inspiration of a patient and the second region of the deflector lies in the stream of gas when inspiration is not occurring.

23. A nebulizer according to claim 22 wherein the deflector is moveable relative to the gas exit.

24. A nebulizer according to claim 23 wherein the deflector includes a deflector edge, the edge including the first and second regions.

25. A nebulizer according to claim 24 wherein the deflector edge is arc-shaped.

26. A nebulizer according to claim 18 wherein the deflector is adjustable towards the gas exit into the non-atomizing configuration.

27. A nebulizer according to claim 18 wherein when the deflector is placed in the non-atomizing position, the increase in the deflection of the portion of the stream of gas disrupts and/or increases the deflection of the whole stream of gas.

28. A method of atomizing a substance comprising:
 (a) providing a substance for atomization;
 (b) providing a deflector having a first profile and second profile, said first and second profiles being different;
 (c) providing a stream of breathable gas;
 (d) passing the stream of breathable gas through a gas exit and deflecting the stream of breathable gas with the deflector;
 (e) changing the profile of the deflector between the first profile, whereby the gas stream is deflected to cause atomization of the substance, and the second profile whereby the gas stream is deflected but does not cause atomization of the substance; and
 (f) providing an outlet through which the stream of breathable gas with or without the atomized substance contained therein may be conducted.

29. A method of atomizing a substance comprising:
 (a) providing a substance for atomization;
 (b) providing a deflector having an atomizing configuration and non-atomizing configuration, said atomizing configuration and non-atomizing configuration being different;
 (c) providing a stream of breathable gas;
 (d) passing the stream of breathable gas through a gas exit and deflecting the stream of breathable gas with the deflector;
 (e) adjusting the deflector between the atomizing configuration in which the deflector lies in the stream of breathable gas for atomization, and the non-atomizing configuration, in which the deflector lies in the stream of breathable gas and increases the deflection of at least a portion of the stream of breathable gas so that no atomization occurs; and
 (f) providing an outlet through which the stream of breathable gas with or without the atomized substance contained therein may be conducted.

* * * * *